United States Patent
Links

(10) Patent No.: US 9,492,317 B2
(45) Date of Patent: Nov. 15, 2016

(54) CASSETTE CAPTURE MECHANISM

(75) Inventor: Jeremy T. Links, Santa Ana, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 12/416,015

(22) Filed: Mar. 31, 2009

(65) Prior Publication Data
US 2010/0249693 A1   Sep. 30, 2010

(51) Int. Cl.
*A61F 9/007* (2006.01)

(52) U.S. Cl.
CPC ..... *A61F 9/00736* (2013.01); *A61M 2205/121* (2013.01)

(58) Field of Classification Search
CPC ............. A61M 2205/12; A61M 2205/50; A61M 2205/502; A61M 2205/3306; A61M 2205/6054; A61M 2205/128; A61M 2205/14; A61M 5/142; A61M 5/172; A61M 39/1011; A61M 16/0816; A61M 1/1601; A61M 1/281; A61M 2209/08; A61M 2005/16863; A61M 1/0058; A61M 1/0031; A61M 2205/123; A61M 1/0025; A61M 1/0072; A61M 1/0076; A61M 2205/10; A61M 2205/3389; A61M 2205/3569; A61M 2205/582; A61M 2205/6018; A61M 2205/6063; A61M 2210/0612; A61M 1/0001; A61M 1/0027; A61M 1/0035; A61M 1/0037; A61M 1/0049; A61M 1/0062; A61M 2205/121; A61M 2205/3331; A61M 2205/3379; A61M 3/0216; A61M 3/0233; A61M 3/0254; A61M 5/01
USPC ............ 604/65, 294, 30, 34, 153; 417/477.2
See application file for complete search history.

(56) References Cited

U.S. PATENT DOCUMENTS

| 1,848,024 A | 3/1932 | Owen |
| 2,123,781 A | 7/1938 | Huber |
| 3,076,904 A | 2/1963 | Claus et al. |
| 3,116,697 A | 1/1964 | Theodore |

(Continued)

FOREIGN PATENT DOCUMENTS

| AU | 2006235983 A1 | 5/2007 |
| DE | 3826414 A1 | 2/1989 |

(Continued)

OTHER PUBLICATIONS

Co-pending U.S. Appl. No. 13/922,475, filed Jun. 20, 2013.

(Continued)

*Primary Examiner* — Bhisma Mehta
*Assistant Examiner* — Brandy S Lee
(74) *Attorney, Agent, or Firm* — Abbott Medical Optics Inc.

(57) ABSTRACT

The present invention pertains to a cassette capture mechanism for uniting a cassette with a console to prevent jamming or damage to the console and/or cassette. The cassette capture mechanism comprises a cassette receptacle, an axial translation linkage, a first sensor apparatus, and a second sensor apparatus. The cassette receptacle is configured to couple with a cassette having a positioning surface. The axial translation linkage is configured to couple the cassette with the cassette receptacle. The first sensor apparatus is configured to detect alignment of the cassette in a horizontal plane with respect to the cassette receptacle when the cassette is initially coupled with the cassette receptacle; and the second sensor apparatus is configured to detect activation of the first sensor apparatus and detect alignment of the cassette in a vertical plane with respect to the cassette receptacle.

14 Claims, 10 Drawing Sheets

(56) References Cited

U.S. PATENT DOCUMENTS

| | | |
|---|---|---|
| 3,439,680 A | 4/1969 | Thomas, Jr. |
| 3,526,218 A | 9/1970 | Lewis |
| 3,781,142 A | 12/1973 | Zweig |
| 3,857,387 A | 12/1974 | Shock |
| 4,017,828 A | 4/1977 | Watanabe et al. |
| 4,037,491 A | 7/1977 | Newbold |
| 4,189,286 A | 2/1980 | Murry et al. |
| 4,193,004 A | 3/1980 | Lobdell et al. |
| 4,276,023 A | 6/1981 | Phillips et al. |
| 4,537,561 A | 8/1985 | Xanthopoulos |
| 4,564,342 A | 1/1986 | Weber et al. |
| 4,590,934 A | 5/1986 | Malis et al. |
| 4,665,621 A | 5/1987 | Ackerman et al. |
| 4,706,687 A | 11/1987 | Rogers et al. |
| 4,757,814 A | 7/1988 | Wang et al. |
| 4,758,220 A * | 7/1988 | Sundblom et al. ............. 604/65 |
| 4,772,263 A | 9/1988 | Dorman et al. |
| 4,773,897 A | 9/1988 | Scheller et al. |
| 4,790,816 A | 12/1988 | Sundblom et al. |
| 4,818,186 A | 4/1989 | Pastrone et al. |
| 4,837,857 A | 6/1989 | Scheller et al. |
| 4,920,336 A | 4/1990 | Meijer |
| 4,921,477 A | 5/1990 | Davis |
| 4,933,843 A | 6/1990 | Scheller et al. |
| 4,941,518 A * | 7/1990 | Williams et al. ................. 141/1 |
| 4,954,960 A | 9/1990 | Lo et al. |
| 4,961,424 A | 10/1990 | Kubota et al. |
| 4,965,417 A | 10/1990 | Massie |
| 4,983,901 A | 1/1991 | Lehmer |
| 4,998,972 A | 3/1991 | Chin et al. |
| 5,006,110 A | 4/1991 | Garrison et al. |
| 5,020,535 A | 6/1991 | Parker et al. |
| 5,026,387 A | 6/1991 | Thomas |
| 5,032,939 A | 7/1991 | Mihara et al. |
| 5,039,973 A | 8/1991 | Carballo |
| 5,091,656 A | 2/1992 | Gahn |
| 5,108,367 A | 4/1992 | Epstein et al. |
| 5,110,270 A | 5/1992 | Morrick |
| 5,125,891 A | 6/1992 | Hossain et al. |
| 5,160,317 A | 11/1992 | Costin |
| 5,195,960 A | 3/1993 | Hossain et al. |
| 5,195,961 A | 3/1993 | Takahashi et al. |
| 5,195,971 A | 3/1993 | Sirhan |
| 5,230,614 A | 7/1993 | Zanger et al. |
| 5,242,404 A | 9/1993 | Conley et al. |
| 5,249,121 A | 9/1993 | Baum et al. |
| 5,268,624 A | 12/1993 | Zanger |
| 5,271,379 A | 12/1993 | Phan et al. |
| 5,282,787 A | 2/1994 | Wortich |
| 5,323,543 A | 6/1994 | Steen et al. |
| 5,342,293 A | 8/1994 | Zanger |
| 5,350,357 A | 9/1994 | Kamen et al. |
| 5,351,676 A | 10/1994 | Putman |
| 5,388,569 A | 2/1995 | Kepley |
| 5,454,783 A | 10/1995 | Grieshaber et al. |
| 5,464,391 A | 11/1995 | DeVale |
| 5,470,211 A | 11/1995 | Knott et al. |
| 5,470,312 A | 11/1995 | Zanger et al. |
| 5,499,969 A | 3/1996 | Beuchat et al. |
| 5,520,652 A | 5/1996 | Peterson |
| 5,533,976 A | 7/1996 | Zaleski et al. |
| 5,549,461 A | 8/1996 | Newland |
| 5,554,894 A | 9/1996 | Sepielli |
| 5,561,575 A | 10/1996 | Eways |
| 5,569,188 A | 10/1996 | Mackool |
| 5,580,347 A | 12/1996 | Reimels |
| 5,591,127 A | 1/1997 | Barwick et al. |
| 5,653,887 A | 8/1997 | Wahl et al. |
| 5,657,000 A | 8/1997 | Ellingboe |
| 5,676,530 A | 10/1997 | Nazarifar |
| 5,676,649 A | 10/1997 | Boukhny et al. |
| 5,676,650 A | 10/1997 | Grieshaber et al. |
| 5,693,020 A | 12/1997 | Rauh |
| 5,697,898 A | 12/1997 | Devine |
| 5,697,910 A | 12/1997 | Cole et al. |
| 5,700,240 A | 12/1997 | Barwick et al. |
| 5,724,264 A | 3/1998 | Rosenberg et al. |
| 5,728,130 A | 3/1998 | Ishikawa et al. |
| 5,733,256 A | 3/1998 | Costin |
| 5,745,647 A | 4/1998 | Krause |
| 5,747,824 A | 5/1998 | Jung et al. |
| 5,777,602 A | 7/1998 | Schaller et al. |
| 5,805,998 A | 9/1998 | Kodama |
| 5,807,075 A | 9/1998 | Jacobsen et al. |
| 5,830,176 A | 11/1998 | Mackool |
| 5,843,109 A | 12/1998 | Mehta et al. |
| 5,859,642 A | 1/1999 | Jones |
| 5,871,492 A | 2/1999 | Sorensen |
| 5,879,298 A | 3/1999 | Drobnitzky et al. |
| 5,883,615 A | 3/1999 | Fago et al. |
| 5,899,674 A | 5/1999 | Jung et al. |
| 5,928,257 A | 7/1999 | Kablik et al. |
| 5,938,655 A | 8/1999 | Bisch et al. |
| 5,983,749 A | 11/1999 | Holtorf |
| 6,002,484 A | 12/1999 | Rozema et al. |
| 6,024,428 A | 2/2000 | Uchikata |
| 6,062,829 A | 5/2000 | Ognier |
| 6,077,285 A | 6/2000 | Boukhny |
| 6,086,598 A | 7/2000 | Appelbaum et al. |
| 6,109,895 A | 8/2000 | Ray et al. |
| 6,117,126 A | 9/2000 | Appelbaum et al. |
| 6,139,320 A | 10/2000 | Hahn |
| 6,150,623 A | 11/2000 | Chen |
| 6,179,829 B1 | 1/2001 | Bisch et al. |
| 6,200,287 B1 | 3/2001 | Keller et al. |
| 6,219,032 B1 | 4/2001 | Rosenberg et al. |
| 6,251,113 B1 | 6/2001 | Appelbaum et al. |
| 6,260,434 B1 | 7/2001 | Holtorf |
| 6,360,630 B2 | 3/2002 | Holtorf |
| 6,368,269 B1 | 4/2002 | Lane |
| 6,411,062 B1 | 6/2002 | Baranowski et al. |
| 6,424,124 B2 | 7/2002 | Ichihara et al. |
| 6,436,072 B1 | 8/2002 | Kullas et al. |
| 6,452,120 B1 | 9/2002 | Chen |
| 6,452,123 B1 | 9/2002 | Chen |
| 6,491,661 B1 | 12/2002 | Boukhny et al. |
| 6,511,454 B1 | 1/2003 | Nakao et al. |
| 6,537,445 B2 | 3/2003 | Muller |
| 6,595,948 B2 | 7/2003 | Suzuki et al. |
| 6,632,214 B2 | 10/2003 | Morgan et al. |
| 6,674,030 B2 | 1/2004 | Chen et al. |
| 6,830,555 B2 | 12/2004 | Rockley et al. |
| 6,852,092 B2 | 2/2005 | Kadziauskas et al. |
| 6,862,951 B2 | 3/2005 | Peterson et al. |
| 6,908,451 B2 | 6/2005 | Brody et al. |
| 6,962,488 B2 | 11/2005 | Davis et al. |
| 6,962,581 B2 | 11/2005 | Thoe |
| 7,011,761 B2 | 3/2006 | Muller |
| 7,012,203 B2 | 3/2006 | Hanson et al. |
| 7,070,578 B2 | 7/2006 | Leukanech et al. |
| 7,073,083 B2 | 7/2006 | Litwin, Jr. et al. |
| 7,087,049 B2 | 8/2006 | Nowlin et al. |
| 7,103,344 B2 | 9/2006 | Menard |
| 7,167,723 B2 | 1/2007 | Zhang |
| 7,169,123 B2 | 1/2007 | Kadziauskas et al. |
| 7,236,766 B2 | 6/2007 | Freeburg |
| 7,236,809 B2 | 6/2007 | Fischedick et al. |
| 7,242,765 B2 | 7/2007 | Hairston |
| 7,244,240 B2 | 7/2007 | Nazarifar et al. |
| 7,289,825 B2 | 10/2007 | Fors et al. |
| 7,300,264 B2 | 11/2007 | Souza |
| 7,316,664 B2 | 1/2008 | Kadziauskas et al. |
| 7,336,976 B2 | 2/2008 | Ito |
| 7,381,917 B2 | 6/2008 | Dacquay et al. |
| 7,439,463 B2 | 10/2008 | Brenner et al. |
| 7,465,285 B2 | 12/2008 | Hutchinson et al. |
| 7,470,277 B2 | 12/2008 | Finlay et al. |
| 7,526,038 B2 | 4/2009 | McNamara |
| 7,591,639 B2 | 9/2009 | Kent |
| 7,731,484 B2 | 6/2010 | Yamamoto et al. |
| 7,776,006 B2 | 8/2010 | Childers et al. |
| 7,811,255 B2 | 10/2010 | Boukhny et al. |
| 7,883,521 B2 | 2/2011 | Rockley et al. |
| 7,921,017 B2 | 4/2011 | Claus et al. |

(56) References Cited

U.S. PATENT DOCUMENTS

| | | |
|---|---|---|
| 7,967,777 B2 | 6/2011 | Edwards et al. |
| 8,070,712 B2 | 12/2011 | Muri et al. |
| 8,075,468 B2 | 12/2011 | Min et al. |
| 2001/0023331 A1 | 9/2001 | Kanda et al. |
| 2001/0047166 A1 | 11/2001 | Wuchinich |
| 2001/0051788 A1 | 12/2001 | Paukovits et al. |
| 2002/0019215 A1 | 2/2002 | Romans |
| 2002/0019607 A1 | 2/2002 | Bui |
| 2002/0045887 A1 | 4/2002 | DeHoogh et al. |
| 2002/0070840 A1 | 6/2002 | Fischer et al. |
| 2002/0098859 A1 | 7/2002 | Murata |
| 2002/0137007 A1 | 9/2002 | Beerstecher |
| 2002/0179462 A1 | 12/2002 | Silvers |
| 2002/0183693 A1 | 12/2002 | Peterson et al. |
| 2003/0073980 A1 | 4/2003 | Finlay et al. |
| 2003/0083016 A1 | 5/2003 | Evans et al. |
| 2003/0108429 A1 | 6/2003 | Angelini et al. |
| 2003/0125717 A1 | 7/2003 | Whitman |
| 2003/0224729 A1 | 12/2003 | Arnold |
| 2003/0226091 A1 | 12/2003 | Platenberg et al. |
| 2004/0037724 A1 | 2/2004 | Haser et al. |
| 2004/0068300 A1 | 4/2004 | Kadziauskas et al. |
| 2004/0092922 A1 | 5/2004 | Kadziauskas et al. |
| 2004/0193182 A1 | 9/2004 | Yaguchi et al. |
| 2004/0212344 A1 | 10/2004 | Tamura et al. |
| 2004/0215127 A1 | 10/2004 | Kadziauskas et al. |
| 2004/0224641 A1 | 11/2004 | Sinn |
| 2004/0253129 A1 | 12/2004 | Sorensen et al. |
| 2005/0054971 A1 | 3/2005 | Steen et al. |
| 2005/0065462 A1 | 3/2005 | Nazarifar et al. |
| 2005/0069419 A1 | 3/2005 | Cull et al. |
| 2005/0070859 A1 | 3/2005 | Cull et al. |
| 2005/0070871 A1 | 3/2005 | Lawton et al. |
| 2005/0095153 A1 | 5/2005 | Demers et al. |
| 2005/0109595 A1 | 5/2005 | Mezhinsky et al. |
| 2005/0118048 A1 | 6/2005 | Traxinger |
| 2005/0130098 A1 | 6/2005 | Warner |
| 2005/0187513 A1 | 8/2005 | Rabiner et al. |
| 2005/0197131 A1 | 9/2005 | Ikegami |
| 2005/0209560 A1 | 9/2005 | Boukhny et al. |
| 2005/0236936 A1 | 10/2005 | Shiv et al. |
| 2005/0245888 A1 | 11/2005 | Cull |
| 2005/0261628 A1 | 11/2005 | Boukhny et al. |
| 2006/0035585 A1 | 2/2006 | Washiro |
| 2006/0036180 A1 | 2/2006 | Boukhny et al. |
| 2006/0041220 A1 | 2/2006 | Boukhny et al. |
| 2006/0046659 A1 | 3/2006 | Haartsen et al. |
| 2006/0078448 A1 | 4/2006 | Holden |
| 2006/0145540 A1 | 7/2006 | Mezhinsky |
| 2006/0219049 A1 | 10/2006 | Horvath et al. |
| 2006/0219962 A1 | 10/2006 | Dancs et al. |
| 2006/0224107 A1 | 10/2006 | Claus et al. |
| 2006/0236242 A1 | 10/2006 | Boukhny et al. |
| 2007/0016174 A1 | 1/2007 | Millman et al. |
| 2007/0049898 A1 | 3/2007 | Hopkins et al. |
| 2007/0060926 A1 | 3/2007 | Escaf |
| 2007/0073214 A1 | 3/2007 | Dacquay et al. |
| 2007/0073309 A1 | 3/2007 | Kadziauskas et al. |
| 2007/0078379 A1 | 4/2007 | Boukhny et al. |
| 2007/0231205 A1 | 10/2007 | Williams et al. |
| 2007/0249942 A1 | 10/2007 | Salehi et al. |
| 2008/0015493 A1 | 1/2008 | Childers et al. |
| 2008/0033342 A1 | 2/2008 | Staggs |
| 2008/0066542 A1 | 3/2008 | Gao |
| 2008/0067046 A1 | 3/2008 | Dacquay et al. |
| 2008/0112828 A1 | 5/2008 | Muri et al. |
| 2008/0114289 A1* | 5/2008 | Muri et al. .............. 604/30 |
| 2008/0114290 A1 | 5/2008 | King et al. |
| 2008/0114291 A1 | 5/2008 | Muri et al. |
| 2008/0114300 A1 | 5/2008 | Muri et al. |
| 2008/0114311 A1* | 5/2008 | Muri et al. ............ 604/294 |
| 2008/0114312 A1 | 5/2008 | Muri et al. |
| 2008/0114372 A1 | 5/2008 | Edwards et al. |
| 2008/0114387 A1 | 5/2008 | Hertweck et al. |
| 2008/0125695 A1 | 5/2008 | Hopkins et al. |
| 2008/0125697 A1 | 5/2008 | Gao |
| 2008/0125698 A1 | 5/2008 | Gerg et al. |
| 2008/0146989 A1 | 6/2008 | Zacharias |
| 2008/0243105 A1 | 10/2008 | Horvath |
| 2008/0262476 A1 | 10/2008 | Krause et al. |
| 2008/0281253 A1 | 11/2008 | Injev et al. |
| 2008/0294087 A1 | 11/2008 | Steen et al. |
| 2008/0312594 A1 | 12/2008 | Urich et al. |
| 2009/0005712 A1 | 1/2009 | Raney |
| 2009/0005789 A1 | 1/2009 | Charles |
| 2009/0048607 A1 | 2/2009 | Rockley |
| 2009/0163853 A1 | 6/2009 | Cull et al. |
| 2010/0185150 A1 | 7/2010 | Zacharias |
| 2010/0280435 A1 | 11/2010 | Raney et al. |
| 2011/0092887 A1 | 4/2011 | Wong et al. |
| 2011/0092924 A1 | 4/2011 | Wong et al. |
| 2011/0092962 A1 | 4/2011 | Ma et al. |
| 2011/0098721 A1 | 4/2011 | Tran et al. |
| 2011/0160646 A1 | 6/2011 | Kadziauskas et al. |
| 2012/0065580 A1 | 3/2012 | Gerg et al. |
| 2013/0245543 A1 | 9/2013 | Gerg et al. |
| 2013/0303978 A1 | 11/2013 | Ross |

FOREIGN PATENT DOCUMENTS

| | | |
|---|---|---|
| EP | 56019 A1 | 7/1982 |
| EP | 424687 A1 | 5/1991 |
| EP | 619993 A1 | 10/1994 |
| EP | 1010437 A1 | 6/2000 |
| EP | 1072285 A1 | 1/2001 |
| EP | 1113562 A1 | 7/2001 |
| EP | 1310267 | 5/2003 |
| EP | 1469440 A2 | 10/2004 |
| EP | 1550406 A2 | 7/2005 |
| EP | 1704839 A1 | 9/2006 |
| EP | 1779879 A1 | 5/2007 |
| EP | 1787606 A1 | 5/2007 |
| EP | 1849443 A1 | 10/2007 |
| EP | 1849444 A1 | 10/2007 |
| EP | 1857128 A1 | 11/2007 |
| EP | 1310267 B1 | 1/2008 |
| EP | 1873501 A1 | 1/2008 |
| EP | 1900347 A1 | 3/2008 |
| EP | 1925274 A2 | 5/2008 |
| EP | 1867349 B1 | 11/2008 |
| ES | 2264369 A1 | 12/2006 |
| GB | 2230301 A | 10/1990 |
| GB | 2352887 A | 2/2001 |
| JP | 57024482 A | 2/1982 |
| JP | S58167333 A | 10/1983 |
| JP | 2008188110 A | 8/2008 |
| WO | WO-9220310 A1 | 11/1992 |
| WO | WO-9315777 A2 | 8/1993 |
| WO | WO 93/17729 | 9/1993 |
| WO | WO 93/24082 | 12/1993 |
| WO | 9405346 A1 | 3/1994 |
| WO | WO-9632144 A1 | 10/1996 |
| WO | WO 98/18507 | 5/1998 |
| WO | WO 99/17818 | 4/1999 |
| WO | WO-0000096 A1 | 1/2000 |
| WO | WO-0070225 A1 | 11/2000 |
| WO | WO-0122696 A1 | 3/2001 |
| WO | WO-0228449 A2 | 4/2002 |
| WO | WO 02/34314 A1 | 5/2002 |
| WO | WO-03102878 A1 | 12/2003 |
| WO | WO-2004096360 A1 | 11/2004 |
| WO | WO-2004114180 A1 | 12/2004 |
| WO | WO 2005/084728 | 9/2005 |
| WO | WO-2005092023 A2 | 10/2005 |
| WO | WO-2005092047 A2 | 10/2005 |
| WO | WO-2006101908 A2 | 9/2006 |
| WO | WO-2006125280 A1 | 11/2006 |
| WO | WO-2007121144 A1 | 10/2007 |
| WO | WO 2007/143677 A2 | 12/2007 |
| WO | WO-2007143797 A1 | 12/2007 |
| WO | WO-2007149637 A2 | 12/2007 |
| WO | WO-2008030872 A1 | 3/2008 |
| WO | WO-2008060859 A1 | 5/2008 |
| WO | WO-2008060902 A1 | 5/2008 |

(56) References Cited

FOREIGN PATENT DOCUMENTS

| WO | WO-2008060995 A1 | 5/2008 |
|----|------------------|--------|
| WO | WO-2010054146 A1 | 5/2010 |
| WO | WO-2010054225 A2 | 5/2010 |
| WO | 2013142009 A1 | 9/2013 |

OTHER PUBLICATIONS

International Preliminary Report on Patentability and Written Opinion for Application No. PCT/US07/084157, mailed on May 12, 2009, 10 pages.
International Search Report for Application No. PCT/US07/084157, mailed on Apr. 1, 2008, 3 pages.
Boyd, "Preparing for the Transition" in: The Art and the Science of Cataract Surgery, Chapter 7, 2001, pp. 93-133.
Definition of "Parameter", Retrieved from the Internet:< URL: http://dictionary.reference.com/browse/parameter>.
English Human Translation of JP57024482 from Feb. 9, 1982.
European Search Report for Application No. EP10164058, mailed on Jun. 25, 2010, 2 pages.
European Search Report for Application No. EP13184138.9, mailed on Oct. 24, 2013, 7 pages.
Examination Report mailed Mar. 28, 2012 for European Application No. EP09791072 filed Jul. 31, 2009, 3 pages.
International Preliminary Report on Patentability and Written Opinion for Application No. PCT/US07/083875, mailed on May 12, 2009. 8 pages.
International Preliminary Report on Patentability and Written Opinion for Application No. PCT/US07/083880, mailed on May 12, 2009. 7 pages.
International Preliminary Report on Patentability and Written Opinion for Application No. PCT/US07/084163, mailed on May 12, 2009. 8 pages.
International Preliminary Report on Patentability and Written Opinion for Application No. PCT/US08/064240, mailed on Nov. 24, 2009. 7 pages.
International Preliminary Report on Patentability and Written Opinion for Application No. PCT/US2006/38978, mailed on Apr. 16, 2008. 8 pages.
International Preliminary Report on Patentability and Written Opinion for Application No. PCT/US2006/39868, mailed on Apr. 16, 2008, 6 pages.
International Preliminary Report on Patentability and Written Opinion for Application No. PCT/US2008/072974, mailed on Feb. 16, 2010, 6 pages.
International Preliminary Report on Patentability and Written Opinion for Application No. PCT/US2009/052473, mailed on Feb. 1, 2011, 7 pages.
International Preliminary Report on Patentability and Written Opinion for Application No. PCT/US2009/063479, mailed on May 10, 2011, 11 pages.
International Preliminary Report on Patentability and Written Opinion for Application No. PCT/US2009/063589, mailed on May 10, 2011. 12 pages.
International Search Report and Written Opinion, mailed Mar. 2, 2010, and International Preliminary Report on Patentability, mailed May 10, 2011. for Application No. PCT/US2009/063482, 13 pages.
International Search Report and Written Opinion, mailed Nov. 2, 2009, and International Preliminary Report on Patentability, mailed Feb. 1, 2011. for Application No. PCT/US2009/052466. 12 pages.
International Search Report and Written Opinion, mailed May 10, 2010, and International Preliminary Report on Patentability, mailed May 10, 2011, for Application No. PCT/US2009/063569, 17 pages.
International Search Report and Written Opinion, mailed Feb. 11, 2010, and International Preliminary Report on Patentability, mailed May 10, 2011, for Application No. PCT/US2009/063486, 13 pages.
International Search Report for Application No. PCT/US07/083875, mailed on May 7, 2008, 4 pages.
International Search Report for Application No. PCT/US07/083880, mailed on May 30, 2008, 4 pages.
International Search Report for Application No. PCT/US07/084163. mailed on Apr. 1, 2008, 3 pages.
International Search Report for Application No. PCT/US08/064240, mailed on Oct. 29, 2008, 3 pages.
International Search Report for Application No. PCT/US08/071704, mailed on Nov. 26, 2008, 3 pages.
International Search Report for Application No. PCT/US08/072974, mailed on Feb. 23, 2009, 2 pages.
International Search Report for Application No. PCT/US2006/38978, mailed on Feb. 27, 2007. 3 pages.
International Search Report for Application No. PCT/US2006/39868, mailed on Nov. 12, 2007, 3 pages.
International Search Report for Application No. PCT/US2009/052473, mailed on Nov. 2, 2009. 3 pages.
International Search Report for Application No. PCT/US2009/063479, mailed on Jun. 11, 2010. 5 pages.
International Search Report for Application No. PCT/US2009/063589, mailed on Jul. 21, 2010, 7 pages.
International Search Report for Application No. PCT/US2013/027728, mailed on Jul. 31, 2013, 9 pages.
Merritt R., et al., Wireless Nets Starting to link Medical Gear [online] 2004 [retrieved on Feb. 12, 2007]. Retrieved from the Internet: <http://WWW.embedded.com/news/embeddedindustry/17200577?_requestid=174370>.
Phacoemulsification, [online] [retrieved on Jul. 1, 2009]. Retrieved from the Internet: <http://en.wikipedia.org/wiki/Phacoemulsification>, 2 pages.
International Search Report and Written Opinion for Application No. PCT/US2014/047055, mailed on Oct. 17, 2014, 11 pages.

\* cited by examiner

CASSETTE CAPTURE MECHANISM

TECHNICAL FIELD OF THE INVENTION

The invention pertains to an improved cassette capture mechanism design for uniting a console with a cassette (or pack) to prevent jamming or damage to the console and/or cassette.

BACKGROUND OF THE INVENTION

Previous cassette capture mechanisms have had problems with properly aligning a pack with the console and jamming of a cassette resulting in damage to the console and/or cassette.

The present invention is generally related to methods, devices, and systems for controlling surgical fluid flows, often during treatment of an eye. In exemplary embodiments, the invention facilitates mounting of a cassette onto a surgical console so as to couple the console with a treatment probe. The cassettes optionally comprising disposable structures having conduit networks for providing both irrigation and aspiration during treatments of anterior and/or posterior chambers of the eye, including phacoemulsification ("phaco") of cataracts, treatment of retinal diseases, and the like.

The optical elements of the eye include both a cornea (at the front of the eye) and a lens within the eye. The lens and cornea work together to focus light onto the retina at the back of the eye. The lens also changes in shape, adjusting the focus of the eye to vary between viewing near objects and far objects. The lens is found just behind the pupil and within a capsular bag, the capsular bag being a thin, relatively delicate structure which separates the eye into anterior and posterior chambers.

With age, clouding of the lens or cataracts is fairly common. Cataracts may form in the hard central nucleus of the lens, in the softer peripheral cortical portion of the lens, or at the back of the lens near the capsular bag. Cataracts can be treated by the replacement of the cloudy lens with an artificial lens. Phacoemulsification systems often use ultrasound energy to fragment the lens and aspirate the lens material from within the capsular bag. This may allow the capsular bag to be used for positioning of the artificial lens, and maintains the separation between the anterior portion of the eye and the vitreous humor in the posterior chamber of the eye.

During cataract surgery and other therapies of the eye, accurate control over the volume of fluid within the eye is highly beneficial. For example, while ultrasound energy breaks up the lens and allows it to be drawn into a treatment probe with an aspiration flow, a corresponding irrigation flow may be introduced into the eye so that the total volume of fluid in the eye does not change excessively. If the total volume of fluid in the eye is allowed to get too low at any time during the procedure, the eye may collapse and cause significant tissue damage. Similarly, excessive pressure within the eye may strain and injure tissues of the eye.

While a variety of specific fluid transport mechanisms have been used in phacoemulsification and other treatment systems for the eyes, aspiration flow systems can generally be classified in two categories: 1) volumetric-based aspiration flow systems using positive displacement pumps (e.g. peristaltic); and 2) vacuum-based aspiration systems using a vacuum source, typically applied to the aspiration flow through an air-liquid interface within a reservoir (e.g. Venturi). Both systems may be incorporated into one treatment system and/or cassette. Cassette systems can be used to couple peristaltic pump drive rotors and/or vacuum systems of the surgical consoles to an eye treatment handpiece, with the flow network conduit of the cassette being disposable to avoid cross-contamination between different patients.

The disposable cassettes provide protection for each patient by avoiding cross-contamination between different patients, however, inserting and removing the disposable cassettes has posed a significant problem for surgeons. On current systems, the problem of jamming has occurred upon inserting and removing the disposable cassette from the console resulting in damage to the console and/or the cassette. Any damage to the console results in required maintenance preventing the surgeons to perform any procedures until it is fixed. Further, damage to the disposable cassette can become costly if it keeps occurring upon insertion of the cassette into the console.

In light of the above, it would be advantageous to provide improved devices, systems, and methods for eye surgery. It would be particularly advantageous if these improvements allowed system users to configure an eye treatment system quickly, accurately, and securely, without requiring the surgical staff to manually apply excessive force and without subjecting the various interfacing components to unnecessary strains, torques, or the like. It would be particularly advantageous if mounting of a cassette onto a console could be performed easily and securely while the cassette is supported by a single hand.

SUMMARY OF THE INVENTION

The present invention pertains to a cassette capture mechanism, comprising a cassette receptacle, wherein the cassette receptacle is configured to couple with a cassette having a positioning surface; an axial translation linkage, wherein the axial translation linkage is configured to couple the cassette with the cassette receptacle; a first sensor apparatus, wherein the first sensor apparatus is configured to detect alignment of the cassette in a horizontal plane with respect to the cassette receptacle when the cassette is initially coupled with the cassette receptacle; and a second sensor apparatus, wherein the second sensor apparatus is configured to detect activation of the first sensor apparatus and detect alignment of the cassette in a vertical plane with respect to the cassette receptacle. The first sensor apparatus may comprise one or more alignment switches, wherein the alignment switch comprises a friction roller and a sensor switch. The second sensor apparatus may comprise a detection switch, wherein the detection switch is configured to detect engagement of the positioning surface of the cassette with the cassette receptacle. The axial translation linkage may comprise two or more latches and wherein the latches may comprise a c-channel configured to capture the cassette. The cassette may comprise one or more flanges configured to couple the cassette with the cassette receptacle via the c-channel. The axial translation linkage may be configured to move the two or more latches substantially simultaneously.

The present invention also pertains to a phacoemulsification system, comprising a cassette, wherein the cassette comprises positioning surfaces; and a console, wherein the console comprises a cassette receptacle, an axial translation linkage, a first sensor apparatus, and a second sensor apparatus. The cassette receptacle may be configured to couple with the positioning surfaces of the cassette. The axial translation linkage may be configured to engage the cassette to couple the cassette with the cassette receptacle. The first sensor apparatus may be configured to detect proper alignment of the cassette when the cassette is initially coupled with the cassette receptacle. The second sensor apparatus may be configured to detect activation of the first sensor apparatus and capture the cassette to hold the cassette in proper alignment with the console with the axial translation linkage.

The present invention also pertains to a method of coupling a cassette with a console of a phacoemulsification system, comprising placing the cassette in close proximity to a cassette receptacle, wherein the cassette receptacle comprises a surface; engaging a first sensor apparatus of the console by inserting the cassette into the cassette receptacle; activating the first sensor apparatus by properly aligning the cassette with the cassette receptacle; activating a second sensor apparatus by pushing the cassette farther into the cassette receptacle such that a positioning surface of the cassette comes in contact with the surface of the cassette receptacle; and engaging an axial translation linkage to capture the cassette within the cassette receptacle of the console.

BRIEF DESCRIPTION OF THE DRAWINGS

The present invention is best understood with reference to the following detailed description of the invention and the drawings in which.

DETAILED DESCRIPTION OF THE INVENTION

Figure 1:
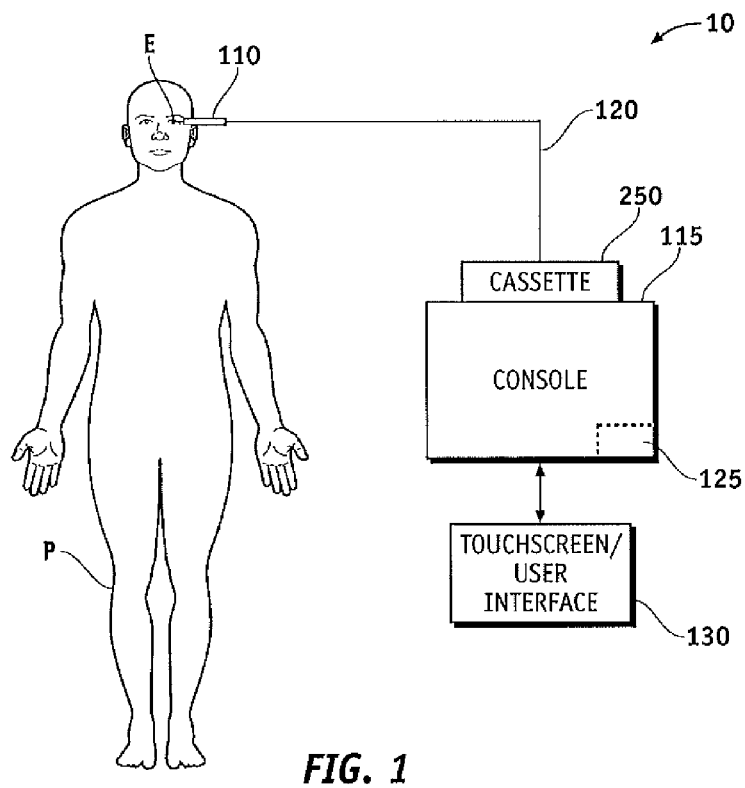
FIG. 1 is a schematic illustrating an eye treatment system in which a cassette is couples an eye treatment probe with an eye treatment console.

Reference will now be made in detail to embodiments of the invention, examples of which are illustrated in the accompanying drawings. While the invention will be described in conjunction with the embodiments, it will be understood that they are not intended to limit the invention to those embodiments. On the contrary, the invention is intended to cover alternatives, modifications, and equivalents, which may be included within the spirit and scope of the invention as defined by the appended claims.

The present invention generally provides improved devices, systems, and methods for surgical treatment. The devices, systems, and methods are generally directed to surgical consoles that incorporate a cassette, for example a fluidics cassette configured to couple the console with a surgical probe or handpiece. Exemplary embodiments provide improved techniques for coupling an eye treatment probe with an eye treatment console by mounting a cassette with the console.

The cassette may include a surgical fluid network, and mounting of the cassette to the console allows various network elements of the cassette to interface with corresponding components of the console. For example, the fluid network of the cassette may include resiliently deformable tubing, a pressure sensor, a reservoir or chamber, and the like. A cassette body may constrain a segment of the tubing in an arcuate configuration, so that when the cassette is mounted to the console a peristaltic drive rotor of the console engages the arc segment of tubing. This allows positive displacement pumping of aspiration fluid from the eye, through the probe, and into a waste receptacle or reservoir. A plurality of peristaltic pumps may be included, with one providing controlled aspiration and the other draining a reservoir or the like. A mixture of flow based pumps and vacuum based pumps may also be employed. Other segments or portions of the resilient tubing of the cassette may be engaged by valve actuators of the console so as to control irrigation and aspiration fluid into and out of the eye via the probe. Many of these interfacing console components and cassette elements may benefit from significant engagement forces to provide robust, accurately aligned, and/or sealed interfacing therebetween.

While embodiments of the present systems may employ manual force to bring the various fluid network elements of the cassette into engagement with the corresponding console components exemplary embodiments will often include a motorized drive linkage that helps move the cassette to the mounted configuration. Many of the interfacing console components benefit from accurately aligned axial movement of the cassette to the mounted position, so that a cassette receptacle of the console may engage positioning surfaces of the cassette so as to inhibit, or render unnecessary, rotation of the cassette during the mounting process. While some embodiments may employ a rotary cassette latching mechanism, maintaining axial movement of the cassette, thus rendering any rotation of the cassette unnecessary, may advantageously limit the angular misalignment between the interfacing structures, potentially providing better sealing or engagement between mating elements and decreasing the stresses and/or undesirable motions between these corresponding structures.

Referring now to FIG. 1, a system 10 for treating an eye E of a patient P generally includes an eye treatment probe handpiece 110 coupled with a console 115 by a cassette 250. Handpiece 110 generally includes a handle for manually manipulating and supporting an insertable probe tip. The probe tip has a distal end which is insertable into the eye, with one or more lumens in the probe tip allowing irrigation fluid to flow from console 115 and/or cassette 250 into the eye. Aspiration fluid may also be withdrawn through a lumen of the probe tip, with console 115 and cassette 250 generally including a vacuum aspiration source, a positive displacement aspiration pump, or both to help withdraw and control a flow of surgical fluids into and out of eye E. As the surgical fluids may include biological materials that should not be transferred between patients, cassette 250 will often comprise a disposable (or alternatively, sterilizable) structure, with the surgical fluids being transmitted through flexible conduits 120 of cassette 250 that avoid direct contact in between those fluids and the components of console 115.

When a distal end of the probe tip of handpiece 110 is inserted into an eye E, for example, for removal of a lens of a patient P with cataracts, an electrical conductor and/or pneumatic line (not shown) may supply energy from console 115 to an ultrasound transmitter of handpiece 110, a cutter mechanism, or the like. Alternatively, handpiece 110 may be configured as an irrigation/aspiration (I/A) and/or vitrectomy handpiece. Also, the ultrasonic transmitter may be replaced by other means for emulsifying a lens, such as a high energy laser beam. The ultrasound energy from handpiece 110 helps to fragment the tissue of the lens, which can then be drawn into a port of the tip by aspiration flow. So as to balance the volume of material removed by the aspiration flow, an irrigation flow through handpiece 110 (or a separate probe structure) may also be provided, with both the aspiration and irrigation flows being controlled by console 115.

To avoid cross-contamination between patients without incurring excessive expenditures for each procedure, cassette 250 and its flexible conduits 120 may be disposable. Alternatively, the flexible conduit or tubing may be disposable, with the cassette body and/or other structures of the cassette being sterilizable. Regardless, the disposable components of cassette 250 are typically configured for use with a single patient, and may not be suitable for sterilization. Cassette 250 will interface with reusable (and often quite expensive) components of console 115, including, but not limited to, peristaltic pump rollers, a Venturi or other vacuum source, a controller 125, and/or the like.

Console 115 may include controller 125, which may include an embedded microcontroller and/or many of the components common to a personal computer, such as a processor, data bus, a memory, input and/or output devices (including a user interface 130 (e.g. touch screen, graphical user interface (GUI), etc.), and the like. Controller 125 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 125 may have (or be coupled with) a recording media reader, or the code may be transmitted to controller 125 by a network connection such as an internet, an intranet, an Ethernet™, a wireless network, or the like. Along with programming code, controller 125 may include stored data for implementing the methods described herein, and may generate and/or store data that records parameters corresponding to the treatment of one or more patients. Many components of console 115 may be found in or modified from known commercial phacoemulsification systems from Abbott Medical Optics, Inc. of Santa Ana, Calif.; Alcon Manufacturing, Ltd. of Ft. Worth, Tex., Bausch and Lomb of Rochester, N.Y., and other suppliers.

Figure 2B:
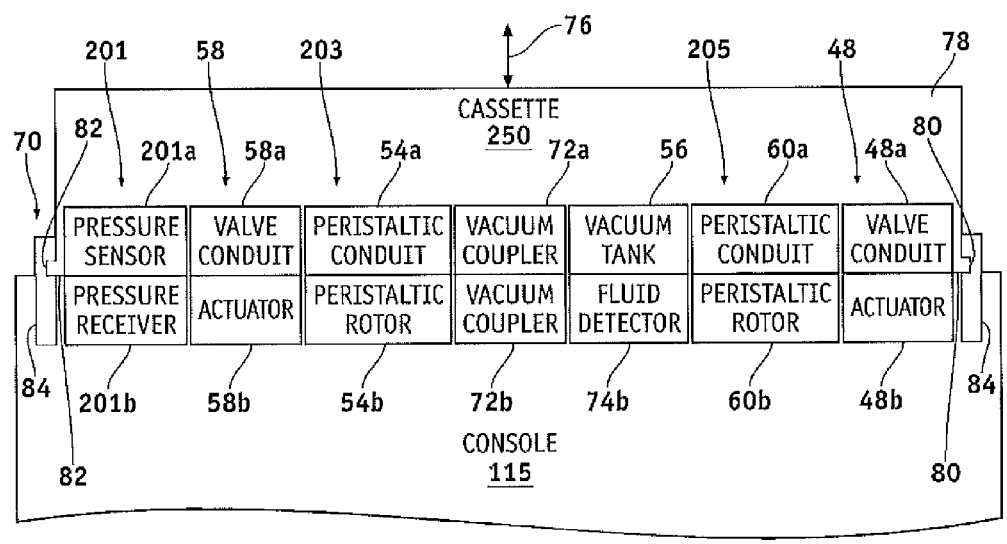
FIG. 2B is a schematic illustrating elements of a cassette and console as shown in FIG. 1.
Figure 2:
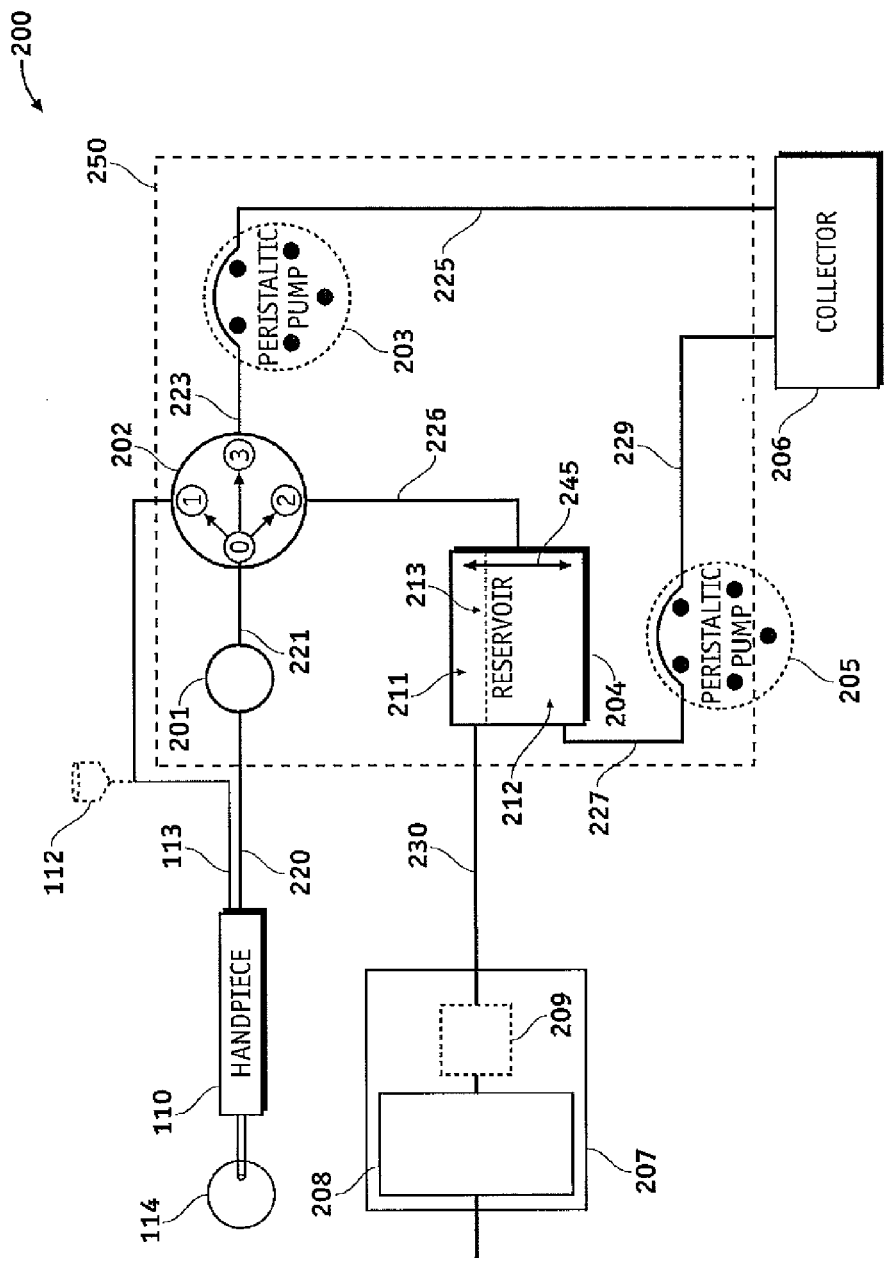
FIG. 2 is a functional block diagram of an exemplary cassette system.

Referring to FIG. 2, an exemplary cassette system showing some of the components and interfaces that may be employed in a phaco system. Handpiece 110 is connected to (or coupled with) the input side of fluid vacuum sensor 201, typically by conduits 120 which comprise fluid pathways such as fluid pathway 220. The output side of fluid vacuum sensor 201 is connected to flow selector valve 202 within cassette 250 via fluid pathway 221. The present design may configure flow selector valve 202 to interface between handpiece 110, balanced saline solution (BSS) fluid bottle 112, pump 203, which is shown as a peristaltic pump but may be another type of pump, and reservoir 204. In this configuration, the system may operate flow selector valve 202 to connect handpiece 110 with BSS fluid bottle 112, reservoir 204 or with pump 203 based on signals received from console 115 resulting from the surgeon's input to user interface 130.

The flow selector valve 202 illustrated in FIG. 2 provides a single input port and may connect port '0' to one of three available ports numbered '1', '2', and '3'. The present design is not limited to one flow selector valve, and may be realized using two flow selector valves each having at least two output ports, possibly connected together to provide the functionality described herein. For example, a pair of two output port valves may be configured in a daisy chain arrangement, where the output port of a first valve is directly connected to the input port of a second valve. Console 115 may operate both valves together to provide three different flow configurations. For example, using two valves, valve one and valve two, valve one may use output port one, which is the supply for valve two. Valve two may connect to one of two ports providing two separate paths. When valve one connects its input port to its second output port rather than the output port that directs flow to the second valve, a third path is provided.

It is also envisioned that flow selector valve 202 may be or comprise one or more pinch valves. The one or more pinch valves may be located along fluid pathway 221 and/or 223, or any other fluid pathway as discussed herein. Further, there may be one or more fluid pathways coupled with handpiece 110 and extending to various components of cassette 250, including a first fluid pathway from fluid vacuum sensor 201 to collector 206 via pump 203 and/or a second fluid pathway to reservoir 204. In another embodiment, fluid pathway 220 is a single fluid pathway that couples with fluid vacuum sensor 201. From fluid vacuum sensor 201, the single fluid pathway 220 may divide into two fluid pathways, one to collector 206 via pump 203 and one to reservoir 204. Further, one or more pinch valves and/or flow selector valve 202 may be located along the fluid pathway between fluid vacuum sensor 201 and collector 206 and/or between fluid vacuum sensor 201 and reservoir 204.

Thus while a single flow selector valve 202 is illustrated in FIG. 2, it is to be understood that this illustration represents a flow selector valve arrangement, including one or more flow selector valves performing the functionality described herein, and is not limited to a single device or a single flow selector valve.

The present design's fluid vacuum sensor 201, for example a strain gauge or other suitable component, may communicate or signal information to console 115 to provide the amount of vacuum sensed in the handpiece fluid pathway 220. Console 115 may determine the actual amount of vacuum present based on the communicated information.

Fluid vacuum sensor 201 monitors flow into and out of the line, and can be used to determine when flow should be reversed, such as encountering a certain pressure level (e.g. in the presence of an occlusion), and based on values obtained from the fluid vacuum sensor 201, the system may control selector valve 202 and the pumps illustrated. It is to be understood that while components presented in FIG. 2 and other drawings of the present application are not shown connected to other system components, such as console 115, they are in fact connected for the purpose of monitoring and control of the components illustrated.

With respect to fluid vacuum sensor 201, emergency conditions such as a dramatic drop or rise in pressure may result in a type of fail-safe operation. The present design employs fluid vacuum sensor 201 to monitor the flow conditions and provide signals representing flow conditions to the system such as via console 115 for the purpose of controlling components shown including but not limited to flow selector valve 202 and the pumps shown.

The fluid pathways or flow segments of surgical cassette system 200 may include the fluid connections, for example flexible tubing, between each component represented with solid lines in FIG. 2.

Vacuum pump arrangement 207 is typically coupled with console 115, and may be connected with reservoir 204 via fluid pathway or flow segment 230. In the configuration shown, vacuum pump arrangement 207 includes a pump 208, such as a venturi pump and an optional pressure regulator 209 (and valve (not shown)), but other configurations are possible. In this arrangement, vacuum pump arrangement 207 may operate to remove air from the top of reservoir 204 and deliver the air to atmosphere (not shown). Removal of air from reservoir 204 in this manner may reduce the pressure within the reservoir, which reduces the pressure in the attached fluid pathway 226, to a level less than the pressure within eye 114. A lower reservoir pressure connected through flow selector valve 202 may cause fluid to move from the eye, thereby providing aspiration. The vacuum pump arrangement 207 and reservoir 204 can be used to control fluid flow into and out of reservoir 204.

The optional pressure regulator 209 may operate to add air to the top of reservoir 204 which in turn increases pressure and may force the air-fluid boundary 213 to move downward. Adding air into reservoir 204 in this manner may increase the air pressure within the reservoir, which increases the pressure in the attached fluid aspiration line 226 to a level greater than the pressure within eye 114. A higher reservoir pressure connected through flow selector valve 203 may cause fluid to move toward eye 114, thereby providing venting or reflux.

The present design may involve peristaltic operation, aspirating fluid from eye 114 to collector 206 illustrated in FIG. 2, or venting fluid to the eye 114 to reduce the amount of pressure in the aspiration line (where such venting is only shown from BSS bottle 112 in FIG. 2). Peristaltic pumping is generally understood to those skilled in the art, and many current machines employ peristaltic and/or venturi pumps as the vacuum or pressure sources. Generally, a peristaltic pump has fluid flowing through a flexible tube and a circular rotor with a number of rollers attached to the periphery of the circular rotor. As the rotor turns, fluid is forced through the tube. Venturi pumping, or aspiration or aspirator pumping, produces the vacuum using the venturi effect by providing fluid through a narrowing tube. Because of the narrowing of the tube, the speed at which the fluid travels through the tube increases and the fluid pressure decreases (the "Venturi effect"). As may be appreciated, operating pumps in one direction or another can change the pressure and the operation of the associated device, such as the operation of the cassette in the present design.

Figure 2A:
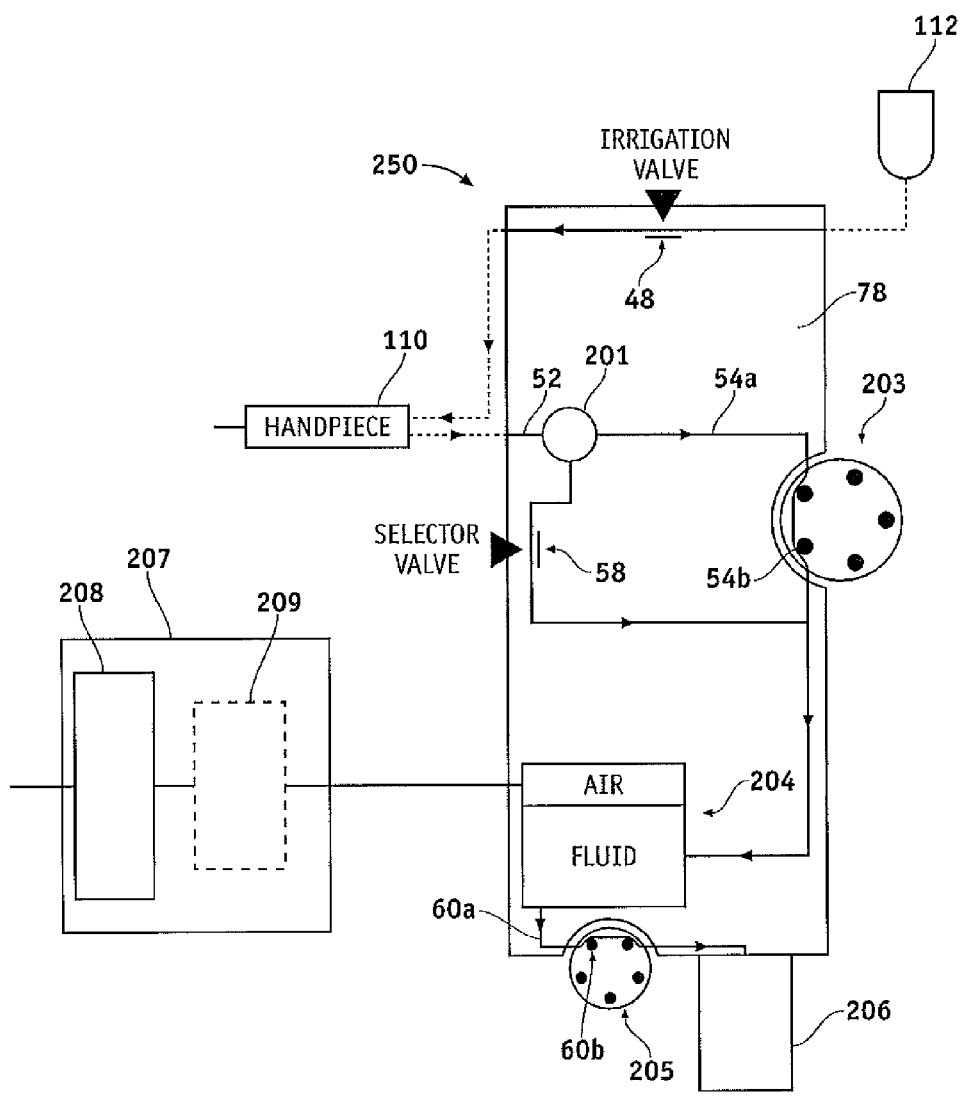
FIG. 2A is a functional block diagram of an exemplary cassette system.

Referring now to FIG. 2A, another system is illustrated. FIG. 2A generally highlights the surgical aspiration and irrigation fluid control elements included within the cassette 250 and console 115, with the irrigation components often being relatively straightforward. A BSS fluid bottle 112 of console 115 optionally provides irrigation fluid pressure control by relying at least in part on a gravity pressure head that varies with a height of BSS fluid bottle 112 or the like. An irrigation on/off pinch valve 48 may generally include a short segment of a flexible conduit of cassette 250, which can be engaged and actuated by an actuator of console 115, with a surface of cassette body 78 often being disposed opposite the actuator to facilitate closure of the conduit lumen. Alternative irrigation flow systems may include positive displacement pumps, alternative fluid pressurization drive systems, fluid pressure or flow modulating valves, as discussed above, and/or the like.

Aspiration flow path 52 couples an aspiration port in the tip of handpiece 110 with pump 203 and/or a reservoir 204. Fluid aspirated through handpiece 110 may be contained in reservoir 204 regardless of whether the aspiration flow is induced by pump 203 or vacuum pump arrangement 207. When valve 58 is closed and pump 203 is in operation, pumping of the aspiration flow may generally be directed by the pump, independent of the pressure in the reservoir 204. The aspiration flow may flow through conduit 54a. Conversely, if pump 203 is a peristaltic pump, when pump 203 is off, flow through the pump may be halted by pinching of the elastomeric tubing arc of the peristaltic pump by one or more of the individual rollers of the peristaltic pump rotor. Hence, any aspiration fluid drawn into the aspiration network (fluid pathways) when pump 203 is off will typically involve the opening of a selector control valve 58 so that the aspiration port of the probe is in fluid communication with reservoir 204. Alternatively, communication with vacuum pump arrangement 207 may be accomplished by disengaging the peristaltic probe drive from the elastomeric tubing. The pressure within reservoir 204 may be maintained at a controlled vacuum level, often at a fixed vacuum level, by vacuum pump arrangement 207. Vacuum pump arrangement 207 may comprise a vacuum (e.g. Venturi) pump, a rotary vane pump, a vacuum source, pressure regulator, or the like. Aspiration fluid that drains into reservoir 204 may be removed by pump 205 and directed to collector 206. Vacuum pressure at the surgical handpiece may be maintained within a desired range through control of the fluid level in reservoir 204.

Referring now to FIG. 2B, an interface 70 between cassette 250 and console 115 is schematically illustrated. Many of the fluid network structure described above regarding FIGS. 2 and 2A include or make use of corresponding elements of cassette 250 and the console 115. For example, with respect to FIG. 2A, fluid vacuum sensor 201 may be included in a pressure sensing system which includes a pressure sensor 201a having a pressure chamber and a surface that moves in response to variations in the pressure in the chamber. Axial movement of the pressure sensor surface may be determined using a pressure receiver 201b. In the exemplary embodiments, direction of movement of the pressure sensor surface may be aligned with a mounting axis 76 of cassette 250, representing a direction of movement of cassette 250 during mounting of cassette 250 to console 115.

Similarly, selector valve 58 may make use of a resilient valve conduit 58a in cassette 250 that is engaged by an actuator 58b of console 115. As described above, pump 203 may include a conduit 54a of cassette 250 engaged by a peristaltic rotor 54b of console 115, with the interface 70 effecting engagement between the conduit 54a and the peristaltic rotor 54b. A vacuum coupler 72a of cassette 250 may engage a vacuum coupler 72b of console 115 so as to allow vacuum pump arrangement 207 to apply a vacuum to reservoir 204 (See FIG. 2A). Reservoir 204 may be coupled with a fluid detector 74b of console 115 using a mechanical, electrical, or light fluid presence detector system so as to allow controller 125 of console 115 to determine when it is appropriate to energize pump 205. Rather than simply detecting the presence of fluid, alternative embodiments might employ a more complex fluid level sensing system which determines a quantity or volume of fluid in the tank for purposes of selectively energizing pump 205. Pump 205 includes a conduit 60a of cassette 250 and a peristaltic rotor 60b of console 115. Irrigation valve 48 may include a resilient valve conduit 48a of cassette 250 and a valve actuator 48b of console 115.

Figure 3:
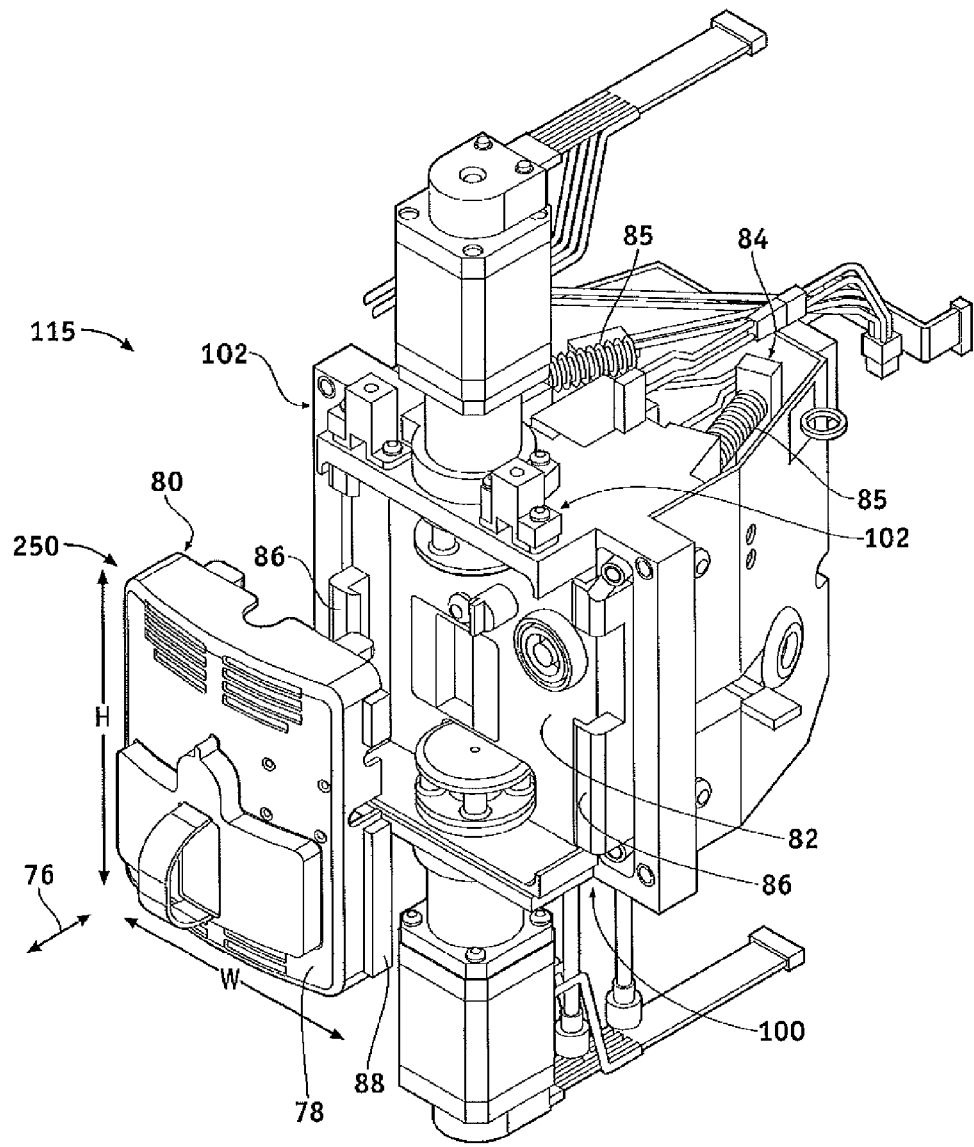
FIG. 3 is a perspective view of a cassette and a cassette receptacle of the console.

Engagement between cassette 250 and the interfacing structures of console 115 can be understood with reference to FIGS. 3-7. Referring to FIG. 3, cassette 250 generally has height H and a width W which generally are greater than a thickness of cassette 250 along mounting axis 76, allowing the interfacing fluid pathway network elements of cassette 250 and corresponding components of console 115 to be distributed in a roughly planner configuration. In addition to the individual interfaces, cassette 250 will generally include a cassette body 78 with positioning surfaces 80 that engage corresponding cassette receptacle surfaces 82 of console 115. Cassette receptacle surfaces 82 define a cassette receptacle 100 that receives and positions cassette 250. In the exemplary embodiment, cassette 250 is manually supported and advanced along mounting axis 76 until positioning surfaces 80 engages and deflects alignment switch 102 of console 115. One or more alignment switches 102 may be used; preferably two alignment switches are employed with cassette receptacle 100 on console 115. Alignment switch 102 may be a pin/flag, optical, magnetic, or any other detection mechanism known in the art.

Figure 4:
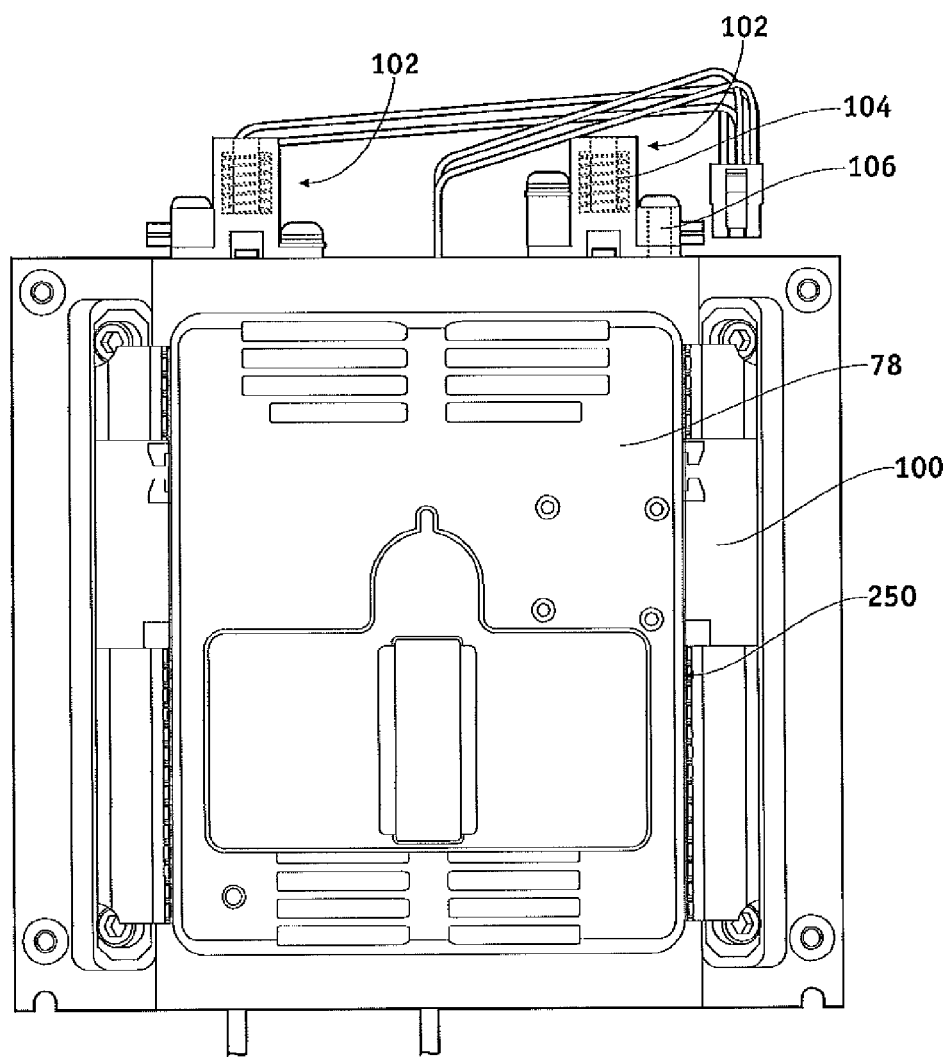
FIG. 4 is a front view showing a cassette coupled with the cassette receptacle of the console.
Figure 5:
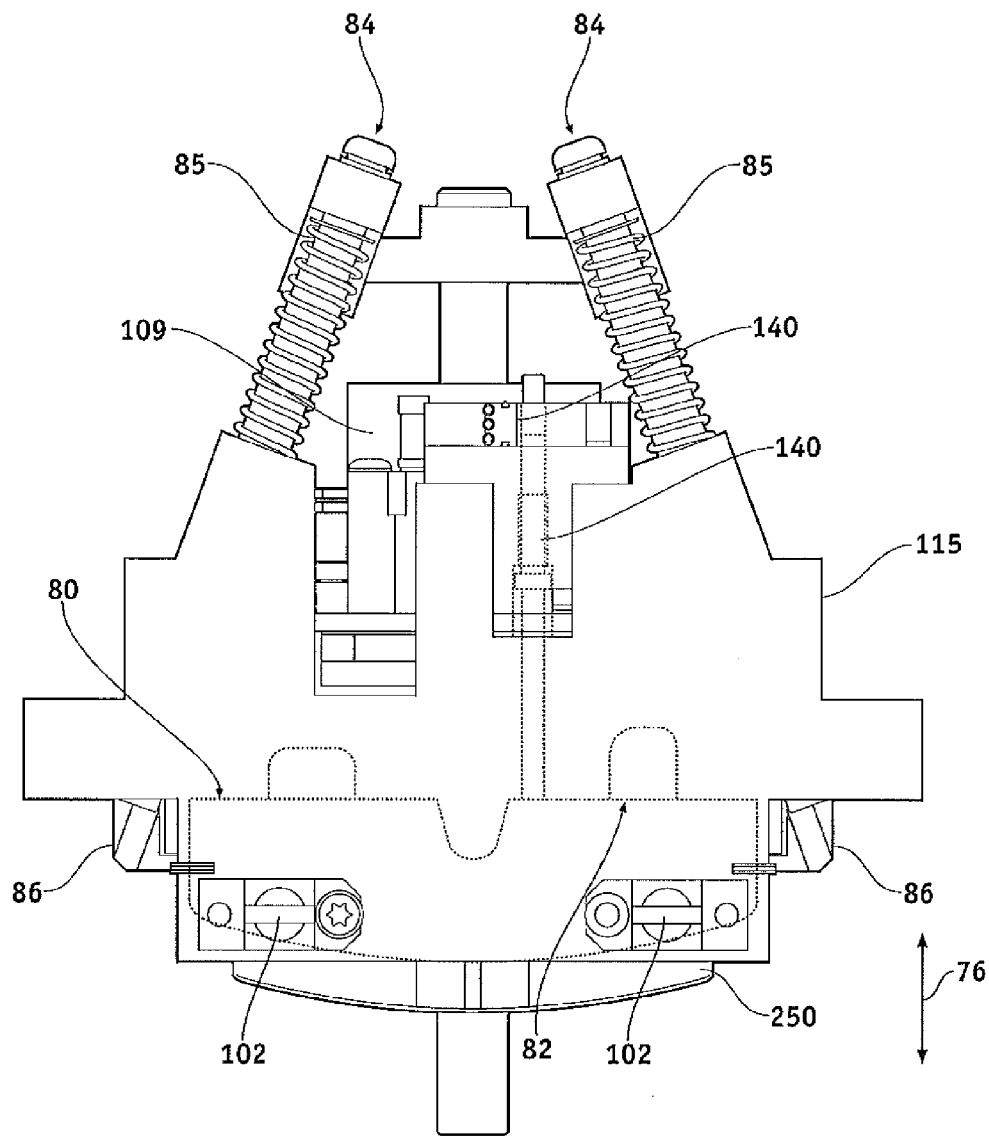
FIG. 5 is a top view showing a cassette coupled with the cassette receptacle of the console.
Figure 6:
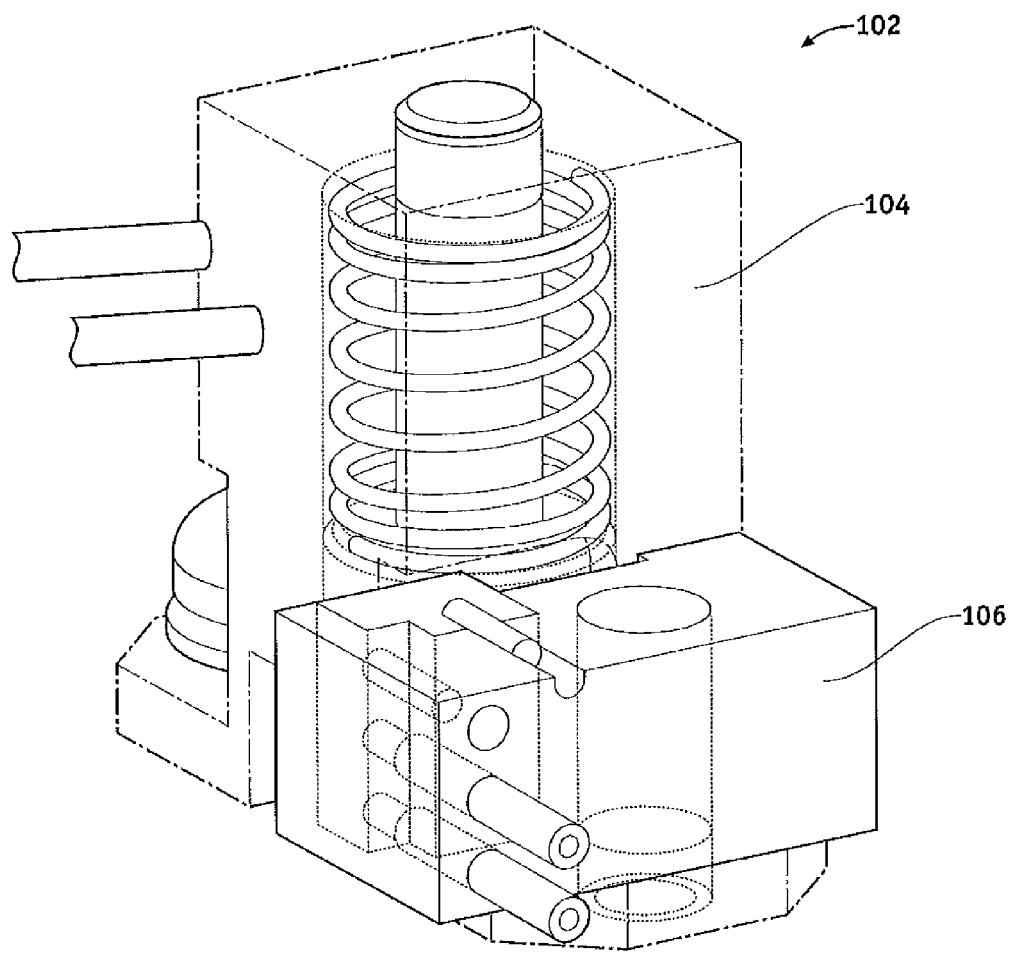
FIG. 6 is a close up view of a pack alignment switch.
Figure 7:
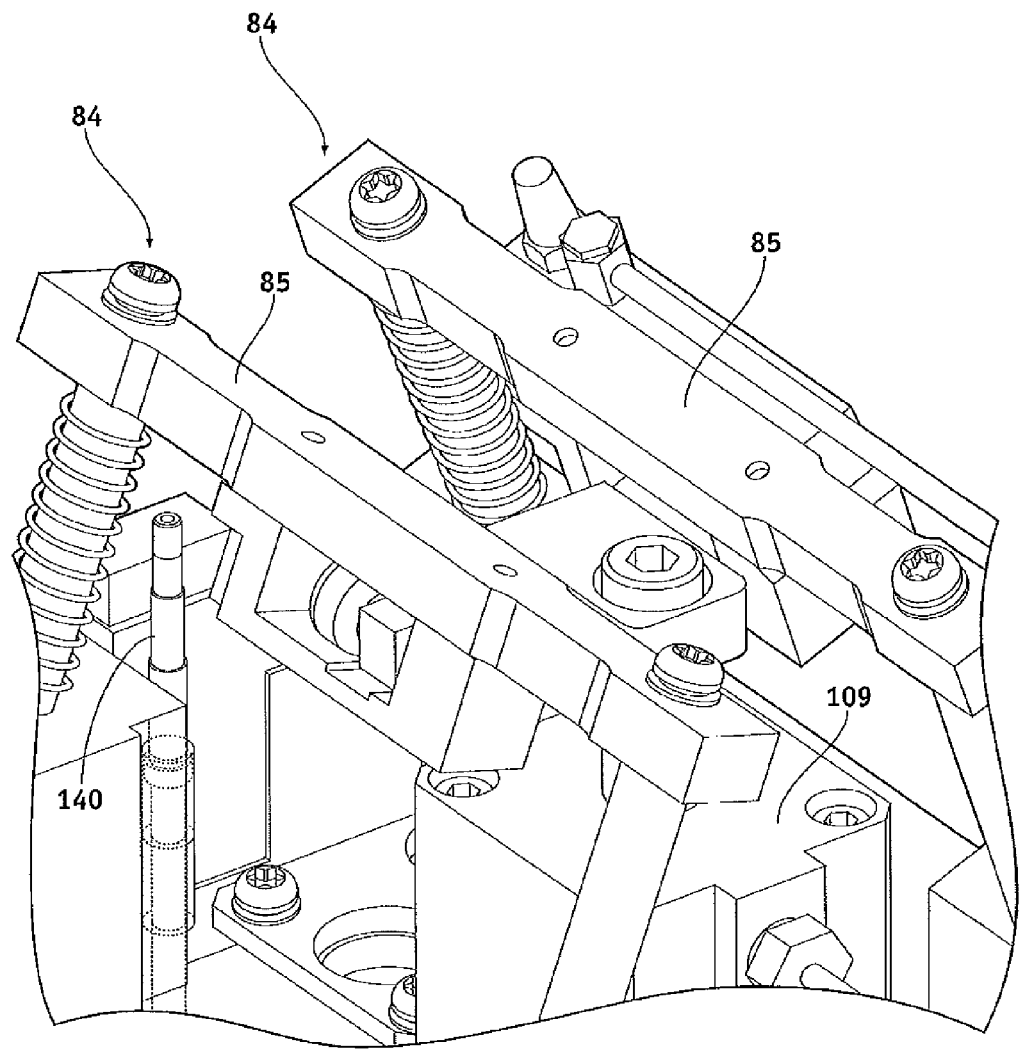
FIG. 7 is a perspective view of the latch mechanism of the cassette receptacle.

Referring to FIGS. 4-7, alignment switch 102 may comprise a friction roller 104 and a sensor switch 106. Sensor switch 106 detects when friction roller 104 has been moved by insertion of cassette 250 into cassette receptacle 100 of console 115. Activation of alignment switch 102 may activate one or more valves of cylinder apparatus 109, which in turn releases air from cylinder 108. Release of air from cylinder 108 enables movement of axial translation linkage mechanism 84. Movement of axial translation linkage mechanism 84 results in substantially simultaneous movement of latches 85, which are coupled with C-channels 86. As illustrated in FIG. 4, alignment switches 102 are shown at the top of cassette receptacle 100, however, one or more alignment switches 102 may be located on the side, bottom, or on surfaces 82 of cassette receptacle 100, or any other configuration known in the art. Cassette receptacle 100 may comprise one or more C-shaped channels (C-channels) 86. More specifically, the inner surfaces of C-channels 86 may receive flanges 88 of cassette 250 therein. According to an embodiment, upon activation of both alignment switches 102 and detection switch 140, C-channels 86 are then drawn towards each other and along axis 76 so as to mount cassette 250 to console 115 by axial translation linkage mechanism 84, which is coupled with C-channels 86.

Detection switch 140 may be coupled with cassette receptacle 100 such that after activation of alignment switches 102 by cassette 250 indicating proper alignment of cassette 250 with cassette receptacle 100, further movement of cassette 250 into cassette receptacle 100 results in cassette 250 triggering detection switch 140. Detection switch 140 may be located anywhere within cassette receptacle 100 as long as positioning surfaces 80 of cassette 250 and detection switch 140 are configured and dimensioned to come in contact with each other. Any type of detection switch known in the art may used with the present invention, including, but not limited to, mechanical contact (e.g. flag switch, lever switch), optical (e.g. photo-interrupter), resistance (e.g. potentiometer), and/or magnetic (e.g. reed switch). Activation of alignment switches 102 causes valve 141 of cylinder apparatus 109 to de-energize enabling further movement of cassette 250 into cassette receptacle 100. Once detection switch 140 is activated, valve 142 of cylinder apparatus 109 pressurizes cylinder 108 enabling axial translation linkage mechanism 84 to move resulting in C-channels 86 to couple with flanges 88 and capture cassette 250. Cylinder apparatus 109 may comprise one or more valves (e.g. valve 141 and valve 142) to assist in the movement of air in and out of cylinder 108. Any device known in the art that functions as a cylinder connection may be used with the present invention, including, but not limited to, an electric solenoid and/or an electric linear actuator. According to an embodiment, activation of axial translation linkage mechanism 84 occurs after activating alignment switches 102 followed by activating detection switch 140. The force necessary to activate cassette receptacle 100 is minimal. Once insertion of cassette 250 is initiated, cylinder apparatus 109 drives axial linkage mechanism 84, which results in forces being properly applied to compress the resilient tubing and/or position the interfacing structures such as valve actuators, the pressure sensor, the peristaltic pump heads, and the like. C-channels 86 may be configured to inhibit rotation of cassette 250 during movement of cassette 250 by axial translation linkage 84.

In another embodiment, cassette receptacle 100 may comprise one or more alignment switches 102 and a capture switch (not shown) located within each C-channel 86. Upon detection of alignment of cassette 250 by activation of one or more alignment switches 102, axial translation linkage mechanism 84 may engage C-channels 86 to move toward each other to capture flanges 88 of cassette 250. Upon detection of flanges 88 by activation of the capture switch, axial translation linkage mechanism 84 continues movement of cassette 250 along mounting axis 76 to couple cassette 250 with cassette receptacle 100 of console 115. The multi-step detection process ensures proper alignment of cassette 250 each time it is inserted to prevent cassette jamming and damage to console 115 and/or cassette 250.

Figure 8:
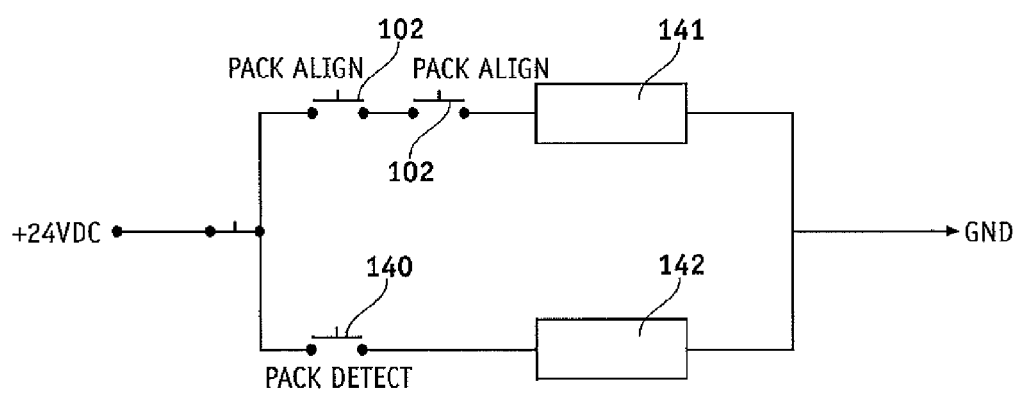
FIG. 8 is an electronic schematic illustrating the pack latching.

FIG. 8 illustrates an electronic schematic of an embodiment of the present invention. Proper alignment of cassette 250 in a horizontal plane activates alignment switches 102, which in turn activate valve 141. Valve 141 de-energizes cylinder 108 of cylinder apparatus 109, enabling cassette 250 to be inserted. Subsequently, activation of detection switch 140 by proper vertical alignment of the cassette 250 with positioning surfaces 80 activates valve 142. Valve 142 energizes cylinder 108 and locks cassette 250 into cassette receptacle 100.

Figure 9:
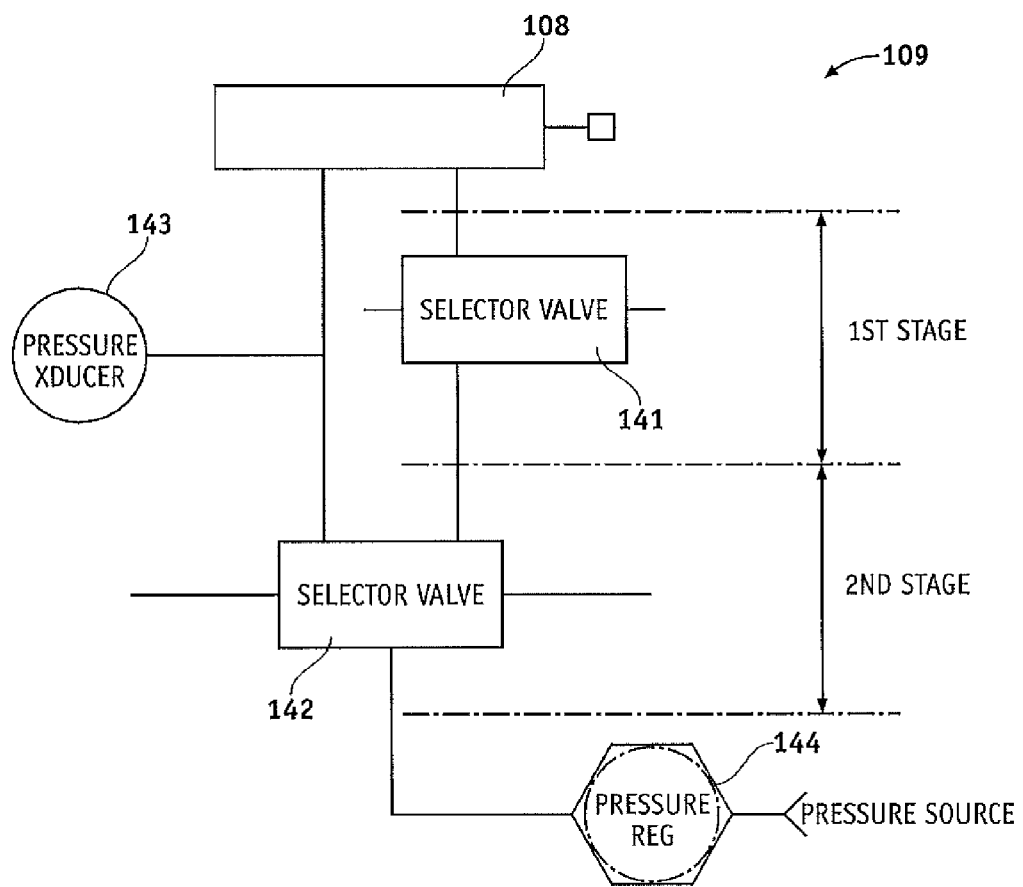
FIG. 9 is a pneumatic schematic illustrating the pack latching.

FIG. 9 illustrates a pneumatic schematic of an embodiment of cylinder apparatus 109. Cylinder apparatus 109 may comprise cylinder 108, pressure transducer 143, pressure regulator 144, and two or more valves, 141 and 142. FIG. 9 shows one valve is activated in each of two stages. Prior to loading cassette 250, cylinder 108 is energized in an open position by valve 141. In the first stage, activation of alignment switches 102 causes valve 141 to de-energize cylinder 108 enabling movement of cassette 250 towards cassette receptacle 100. In stage two, activation of detection switch 140 causes valve 142 to energize cylinder 108 to a closed position. Pressure transducer 143 monitors the amount of air pressure in cylinder 108 and pressure regulator 144 adjusts the amount of air pressure in cylinder 108 depending upon the position of cassette 250 with respect to cassette receptacle 100 and whether alignment switches 102 and/or detection switch 140 are activated.

Although the present invention has been described in terms of specific embodiments, changes and modifications can be carried out without departing from the scope of the invention which is intended to be limited only by the scope of the claims.

The invention claimed is:

1. A cassette capture mechanism, comprising:
a cassette receptacle, wherein the cassette receptacle is configured to couple with a cassette having a positioning surface;
an axial translation linkage, wherein the axial translation linkage is configured to couple the cassette with the cassette receptacle;
a first sensor apparatus, wherein the first sensor apparatus is configured to detect alignment of the cassette in a horizontal plane with respect to the cassette receptacle when the cassette is initially coupled with the cassette receptacle; and
a second sensor apparatus, wherein the second sensor apparatus is configured to detect activation of the first sensor apparatus and facilitate the alignment of the cassette in a vertical plane with respect to the cassette receptacle by causing the axial translation linkage to draw multiple latches towards the cassette receptacle and towards each other substantially simultaneously.

2. The cassette capture mechanism of claim 1, wherein the first sensor apparatus comprises one or more alignment switches, wherein the alignment switch comprises a friction roller and a sensor switch.

3. The cassette capture mechanism of claim 1, wherein the second sensor apparatus comprises a detection switch, wherein the detection switch is configured to detect engagement of the positioning surface of the cassette with the cassette receptacle.

4. The cassette capture mechanism of claim 1, wherein each latch comprises a c-channel configured to capture the cassette.

5. The cassette capture mechanism of claim 4, wherein the cassette comprises one or more flanges configured to couple the cassette with the cassette receptacle via the c-channel.

6. The cassette capture mechanism of claim 1, further comprising a cylinder apparatus, wherein the cylinder apparatus is coupled with the axial translation linkage and configured to move the axial translation linkage to capture the cassette in the cassette receptacle.

7. The cassette capture mechanism of claim 6, wherein the cylinder apparatus comprises a cylinder, a pressure regulator, a pressure transducer, and two or more valves.

8. A phacoemulsification system, comprising
a cassette, wherein the cassette comprises positioning surfaces; and
a console, wherein the console comprises a cassette receptacle, an axial translation linkage, a first sensor apparatus, and a second sensor apparatus,
wherein the cassette receptacle is configured to couple with the positioning surfaces of the cassette;
wherein the axial translation linkage is configured to engage the cassette to couple the cassette with the cassette receptacle;
wherein the first sensor apparatus is configured to detect proper alignment of the cassette when the cassette is initially coupled with the cassette receptacle;
and wherein the second sensor apparatus is configured to detect activation of the first sensor apparatus and capture the cassette to hold the cassette in proper alignment with the console using the axial translation linkage by drawing two or more latches towards the cassette receptacle and towards each other substantially simultaneously.

9. The phacoemulsification system of claim 8, wherein the first sensor apparatus comprises one or more alignment switches, wherein the alignment switch comprises a friction roller and a sensor switch.

10. The phacoemulsification system of claim 8, wherein the second sensor apparatus comprises a detection switch, wherein the detection switch is configured to detect engagement of the positioning surface of the cassette with the cassette receptacle.

11. The phacoemulsification system of claim 8, wherein each latch comprises a c-channel configured to capture the cassette.

12. The phacoemulsification system of claim 11, wherein the cassette comprises one or more flanges configured to couple the cassette with the cassette receptacle via the c-channel.

13. The phacoemulsification system of claim 8, wherein the console further comprises a cylinder apparatus, wherein the cylinder apparatus is coupled with the axial translation linkage and configured to move the axial translation linkage to capture the cassette in the cassette receptacle.

14. The cassette capture mechanism of claim 13, wherein the cylinder apparatus comprises a cylinder, a pressure regulator, a pressure transducer, and two or more valves.

* * * * *